US007400314B1

(12) United States Patent
Agano

(10) Patent No.: US 7,400,314 B1
(45) Date of Patent: Jul. 15, 2008

(54) DISPLAY DEVICE

(75) Inventor: Toshitaka Agano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 09/492,300

(22) Filed: Jan. 27, 2000

(30) Foreign Application Priority Data

Jan. 27, 1999 (JP) ............................. 11-018128

(51) Int. Cl.
*G09G 3/36* (2006.01)
(52) U.S. Cl. .................... 345/102; 345/63; 345/77; 345/211; 345/214; 349/61; 349/65; 349/68; 349/70
(58) Field of Classification Search ............ 345/102, 345/589, 690, 63, 89, 211, 77; 315/224; 349/61
See application file for complete search history.

(56) References Cited

U.S. PATENT DOCUMENTS

| | | | | |
|---|---|---|---|---|
| 4,733,229 A | * | 3/1988 | Whitehead | 340/723 |
| 5,144,292 A | * | 9/1992 | Shiraishi et al. | 340/784 |
| 5,315,695 A | * | 5/1994 | Saito et al. | 345/102 |
| 5,461,397 A | * | 10/1995 | Zhang et al. | 345/102 |
| 5,570,108 A | * | 10/1996 | McLaughlin et al. | 345/146 |
| 5,598,565 A | * | 1/1997 | Reinhardt | 713/323 |
| 5,734,362 A | * | 3/1998 | Eglit | 345/89 |
| 5,737,506 A | * | 4/1998 | McKenna et al. | 395/125 |
| 5,786,801 A | * | 7/1998 | Ichise | 345/102 |
| 5,796,382 A | * | 8/1998 | Beeteson | 345/102 |
| 5,808,597 A | * | 9/1998 | Onitsuka et al. | 345/102 |
| 5,854,617 A | * | 12/1998 | Lee et al. | 345/102 |
| 5,856,817 A | * | 1/1999 | Matsuzaki | 345/98 |
| 5,892,840 A | * | 4/1999 | Jang et al. | 382/132 |
| 5,986,662 A | * | 11/1999 | Argiro et al. | 345/424 |
| 6,020,944 A | * | 2/2000 | Hoshi | 349/62 |
| 6,063,030 A | * | 5/2000 | Vara et al. | 600/437 |
| 6,144,164 A | * | 11/2000 | Ito | 315/169.3 |
| 6,151,008 A | * | 11/2000 | Zhang | 345/102 |
| 6,184,861 B1 | * | 2/2001 | Callway | 345/690 |
| 6,232,963 B1 | * | 5/2001 | Tew et al. | 345/204 |
| 6,269,565 B1 | * | 8/2001 | Inbar et al. | 40/361 |
| 6,424,996 B1 | * | 7/2002 | Killcommons et al. | 709/206 |
| 6,532,474 B2 | * | 3/2003 | Iwamoto et al. | 707/104.1 |
| 6,809,776 B1 | * | 10/2004 | Simpson | 348/565 |
| 2002/0000995 A1 | | 1/2002 | Sawada et al. | |
| 2003/0001856 A1 | * | 1/2003 | Sawada et al. | |

FOREIGN PATENT DOCUMENTS

| | | |
|---|---|---|
| JP | 2-19827 A | 1/1990 |
| JP | 10-214075 A | 8/1998 |
| JP | 10-326091 A | 12/1998 |

* cited by examiner

*Primary Examiner*—Richard Hjerpe
*Assistant Examiner*—Jennifer T Nguyen
(74) *Attorney, Agent, or Firm*—Sughrue Mion, PLLC

(57) ABSTRACT

The display device has at least two set of maximum luminances including an image maximum luminance for displaying an image and an ordinary maximum luminance for displaying non-image information, the ordinary maximum luminance being lower than the image maximum luminance. The display device is capable of display at the appropriate brightness depending on the graphics to be displayed (whether it is an image or non-image information such as characters and menus) or in accordance with the operation done by the viewer (or operator) and which, when used as a monitor for medical diagnostic apparatus, allows for correct diagnosis by bright enough diagnostic images with good operability but without imposing any undue stress on the viewer's eyes.

35 Claims, 3 Drawing Sheets

DISPLAY DEVICE

BACKGROUND OF THE INVENTION

This invention relates to the technical field of display devices such as a liquid-crystal display and a CRT (cathode-ray tube), more particularly to a display device optimal for use as a monitor for medical diagnostic apparatus.

The diagnostic images taken with medical diagnostic apparatus such as MRI diagnostic apparatus, X-ray diagnostic apparatus and apparatus for CR (computed radiography) diagnostic apparatus, for example, FCR (Fuji Computed Radiography made of Fuji Photo Film Co., Ltd.) are usually recorded on light-transmitting image recording films such as X-ray films and light-sensitive materials in film form and thereafter reproduced as light-transmissive images. The films showing the reproduced diagnostic images are set on a light source device called a "Schaukasten" and illuminated with a backlight so that the images are viewed for diagnostic purposes.

Medical diagnostic apparatus usually have a monitor (display) such as CRT, either built-in or connected, for viewing the diagnostic images taken with the apparatus. Diagnosis is performed on the basis of the image output to the monitor or the diagnostic images to be output on films are checked, adjusted or otherwise processed on the monitor.

The diagnostic images displayed on the monitor are usually monochromatic (in black and white) and, in principle, diagnosis is based on the difference in image density. To achieve correct diagnosis, it is required that subtle differences in density be finely identified even if the diagnostic image reproduced on a film has high densities in excess of 2.0. To meet this requirement, the "Schaukasten" (lantern slide) emits very bright light. Monitors for medical diagnostic apparatus are also required to be capable of displaying comparably sharp images and, to this end, very bright display is performed.

However, the diagnostic images are not the only representations on the monitor for medical diagnostic apparatus and usually non-image representations such as characters for the name of the image (file name) and menus (e.g., tool bars and windows) for executing various operations by GUI (graphical user interface) are also displayed. For some operational reasons, only characters and menus may be displayed. If characters and menus are unduly bright, visibility is impaired to reduce the efficiency in operation; what is more, great stress is imposed on the viewer's eyes.

Some monitors have a device for adjusting the brightness of the display but this is in most cases manual and only adapted to perform continuous adjustment in brightness; hence, it is poor in operability.

SUMMARY OF THE INVENTION

The present invention has been accomplished under these circumstances and has as an object providing a display device which is capable of display at the appropriate brightness depending on the graphics to be displayed (whether it is an image or non-image information such as characters and menus) or in accordance with the operation done by the viewer (or operator) and which, when used as a monitor for medical diagnostic apparatus, allows for correct diagnosis by bright enough diagnostic images with good operability but without imposing any undue stress on the viewer's eyes.

This object of the invention can be attained by a display device, having at least two set of maximum luminances, including an image maximum luminance for displaying an image and an ordinary maximum luminance for displaying non-image information, the ordinary maximum luminance being lower than the image maximum luminance.

Preferably, the display device further having a luminance adjusting unit which, when the non-image information is displayed in cases of display of only the image, or display of a mixture of the image and the non-image information, or display of only the non-image information, adjusts a brightness of the display in an area of the non-image information or in an entire display screen in accordance with the ordinary maximum display luminance.

It is also preferred that the display device further having a luminance switching unit which switches a brightness of display in an entire display screen to either adjustment depending on the ordinary maximum luminance or adjustment depending on the image maximum luminance.

Preferably, the luminance switching unit has a selection unit which makes adjustment to the brightness of the display depending on the image maximum luminance in a case of display of only the image and makes adjustment to the brightness of display depending on the ordinary maximum luminance in a case of display of only the non-image information and which also selects the brightness of display depending on the ordinary maximum luminance and the brightness of display depending on said image maximum luminance.

It is also preferred that an entire display screen is adjusted to a brightness of display not higher than the ordinary maximum luminance in accordance with an operation using graphical user interface.

In yet another preferred embodiment, adjustment of a brightness of display in relation to the ordinary maximum luminance and the image maximum luminance is performed by adjustment of either a light source for display or image data or both.

DETAILED DESCRIPTION OF THE INVENTION

On the pages that follow, the display device of the invention is described in detail with reference to the preferred embodiments shown in the accompanying drawings.

Figure 1:
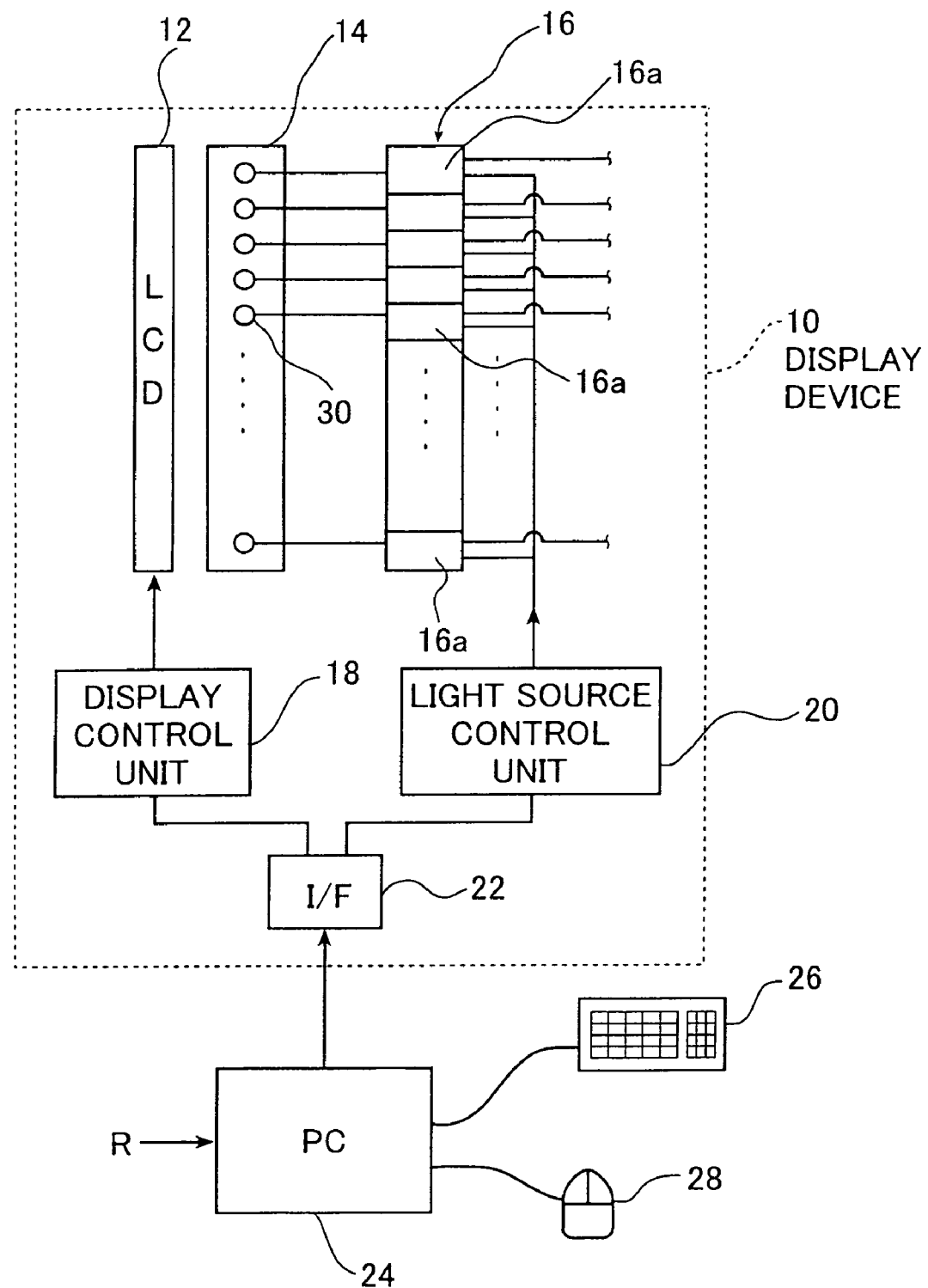
FIG. 1 shows in conceptual form an embodiment of the display device of the invention which is used as a monitor for a medical diagnostic apparatus.

FIG. 1 shows in conceptual form an embodiment of the invention in which the claimed display device is used as a monitor for a medical diagnostic apparatus. The display device generally indicated by 10 in FIG. 1 is a liquid-crystal display device (hereunder referred to as LCD) and comprises a liquid-crystal panel 12 that displays images by liquid crystal as a display unit, a backlight unit 14, a light source drive unit 16 for the backlight unit 14, a display control unit 18, a light source control unit 20, and an interface 22 (hereunder referred to as I/F 22).

I/F 22 in the display device 10 is connected to a personal computer (hereunder referred to as PC) 24 which, in turn, is connected to a medical diagnostic apparatus (hereunder referred to simply as diagnostic apparatus) R such as an X-ray CT diagnostic apparatus, an MRI diagnostic apparatus, an X-ray diagnostic apparatus or CR diagnostic apparatus that are sources of diagnostic images to be represented on the display device 10 and from which image data and so forth are supplied to the PC 24.

PC 24 is also connected to a keyboard 26 and mouse 28 for executing operations by graphical user interface (hereunder abbreviated as GUI) or which are manipulated to input various conditions.

The display device of the invention is by no means limited to the illustrated LCD and all known types of display device, whether they are light-emissive or not, may be employed as long as they are display units which can display images and non-image information, as exemplified by a digital micromirror device (DMD) display, an electrochromic display (ECD), an electrophoretic image display (EPID), a CRT, a plasma display (PDP), a vacuum fluorescence display (VFD), a light-emitting diode (LED) display, an electroluminescent (EL) display, a field emission display (FED) and an organic EL display.

In the LCD utilizing the concept of the invention, the liquid-crystal display 12 is not limited to any particular type and all known liquid-crystal panels that are used in various kinds of LCDs may be employed as long as they have a liquid crystal sandwiched between two spaced transparent supports, which are overlaid with transparent electrodes to produce a sheet assembly having an analyzer on one side and a polarizer on the other side.

Hence, the liquid-crystal panel 12 (the display device 10 of the invention) may be a full-color or monochromatic type and can be operated in all known modes including a TN (twisted nematic) mode, a STN (supertwisted nematic) mode, an ECB (electrically controlled birefringence) mode, an IPS (in-plane switching) mode and a MVA (multi-domain vertical alignment) mode. The liquid-crystal panel 12 also has no limitations on the switching device or the matrix.

In order to widen the viewing angle of the LCD in the display device 10 of the invention, a diffusing plate may optionally be placed on the viewing side of the liquid-crystal panel 12 and a collimating plate on the other side.

The drive (for display purposes) of the liquid-crystal panel 12 is controlled by the display control unit 18, which is connected to PC 24 via I/F 22 and supplied with various kinds of data for display purposes.

The backlight unit 14 is a site for backlighting the LCD or the display device 10 and is composed of multiple light sources 30. The light sources 30 are not limited in any particular way and various types of backlight for known LCDs (non-emissive displays) may be employed. In the illustrated case, the light sources 30 are preferably cold-cathode fluorescent lamps and other tubes that allow for control in the quantity of light by the adjustment of current being supplied.

The respective light sources 30 are driven (turned on) by their respective drivers 16a of the light source drive unit 16. As just mentioned above, the light sources 30 can individually be controlled in the quantity of light by adjusting the current supplied from the drivers 16a. The drivers 16a are connected to the light source control unit 20 which controls the current being supplied from the drivers 16a to the respective light sources 30.

The light source control unit 20 is connected to PC 24 via I/F 22 which is supplied with the necessary data for adjustment of the quantity of light and for other purposes.

Having the basic composition described above, the display apparatus 10 of the invention is characterized in that it has two maximum luminance settings, the first for the display of images (multi-gradation images) such as diagnostic images that were taken with the diagnostic apparatus R and the second for the display of other representations (that is, non-image information) such as characters, menus (e.g., various kinds of menu such as a control menu and a pull-down menu, various kinds of bar such as a title bar and a tool bar, and various kinds of windows such as a first-level window and a dialog box), and the background (desktop) which is a bottom layer of a display screen. The first setting is the image maximum luminance suitable for the display of images and the second setting is the ordinary maximum luminance suitable for the display of other representations such as characters and menus. Images can be displayed at a brightness determined by the image maximum luminance whereas characters and menus can be displayed at a brightness determined by the ordinary maximum luminance. The ordinary maximum luminance is set to be lower than the image maximum luminance. Therefore, in the display device 10 of the invention, characters and menus are in principle displayed at a lower brightness than images.

Thus, by means of the display device 10 of the invention, diagnostic images are displayed at a sufficiently high brightness to enable correct diagnosis whereas the other areas of the display screen are represented at a brightness as appropriate for the non-image information such as menus, characters and others that appears on the display screen in response to an operation by the viewer (operator); as a result, correct diagnosis based on the bright diagnostic images can be performed with satisfactory visibility and maneuverability but without undue stress on the viewer's eyes.

Figure 2:
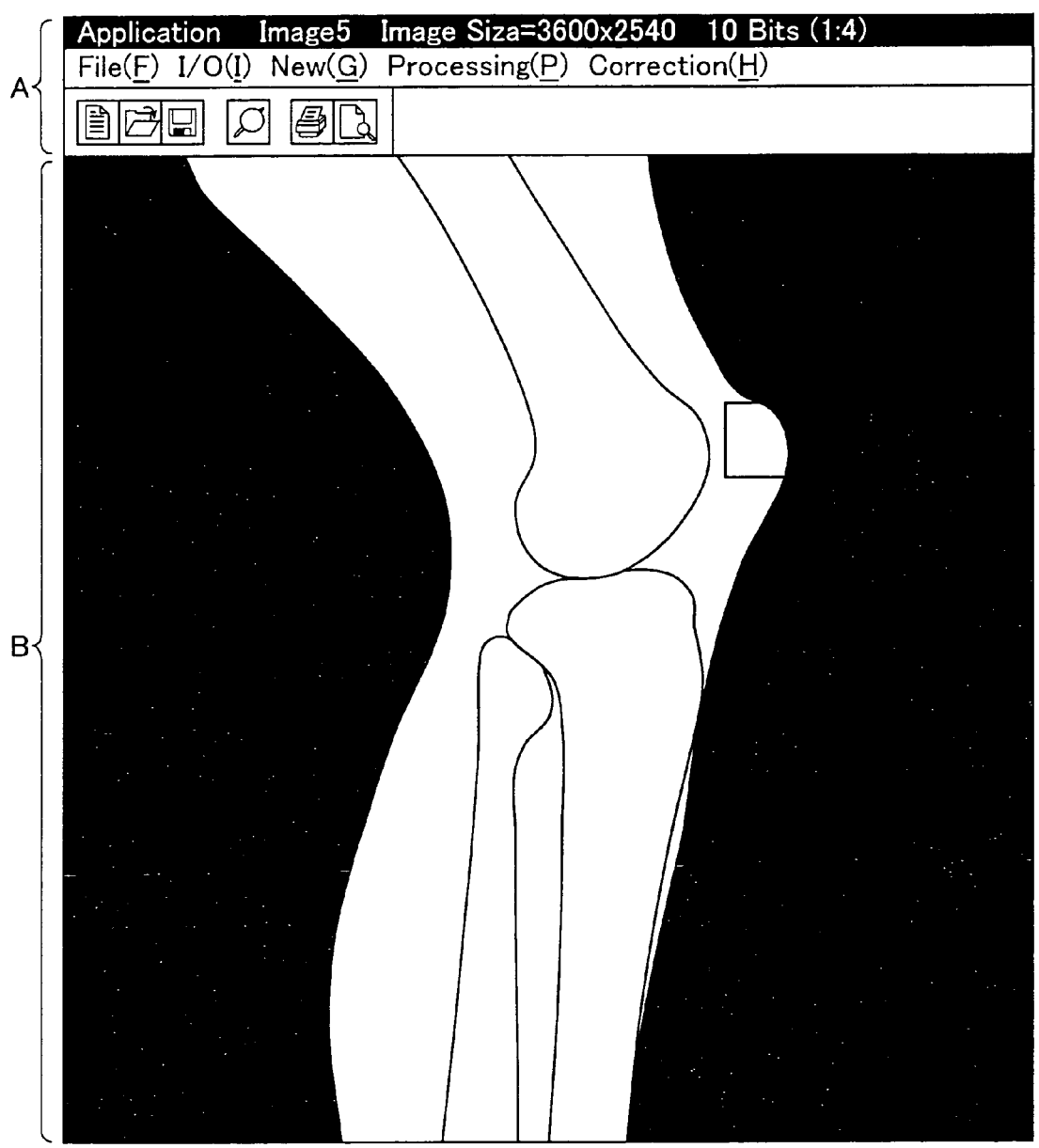
FIG. 2 shows an exemplary display screen from the display device shown in FIG. 1.
Figure 3:
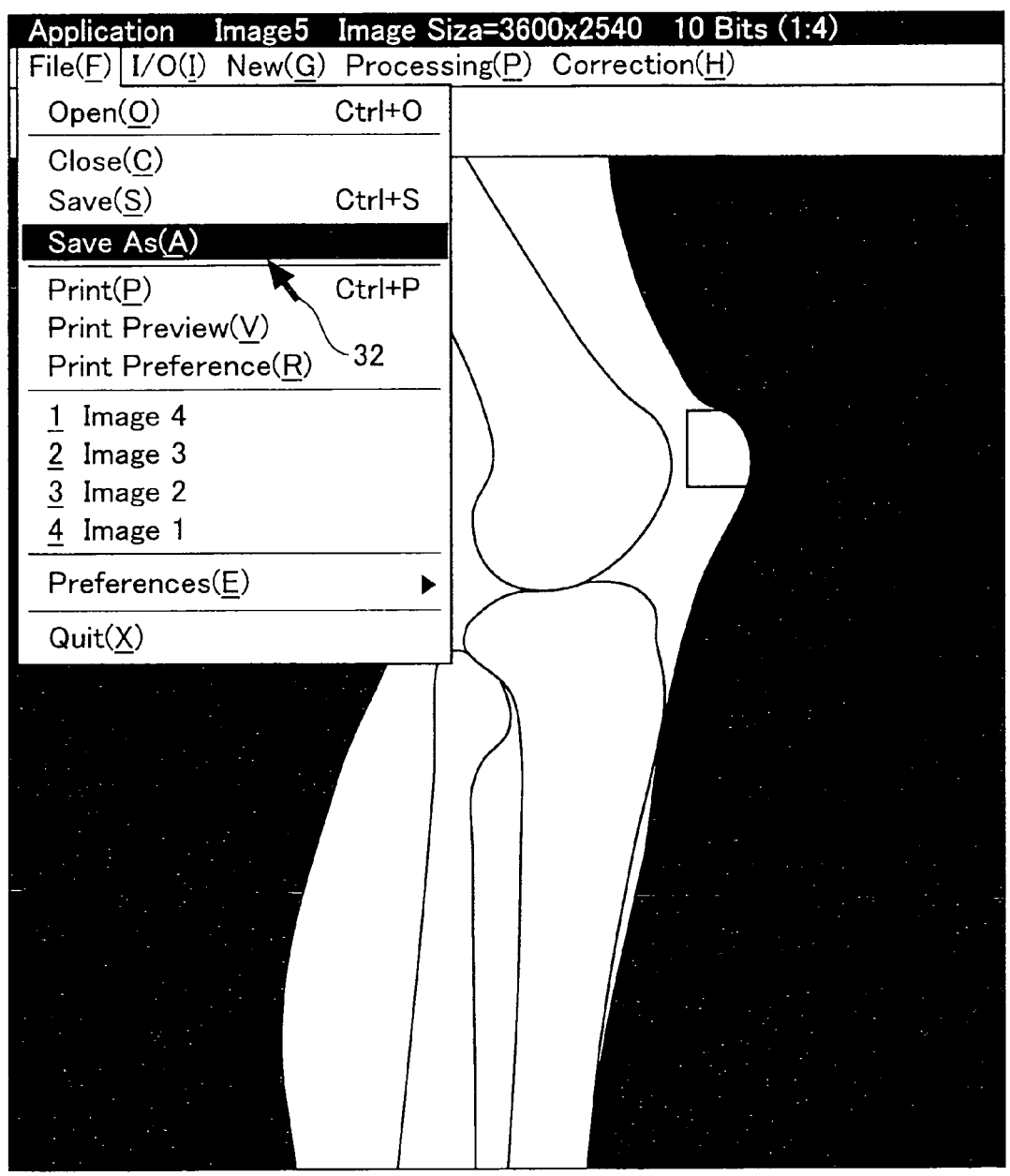
FIG. 3 shows an exemplary screen display represented after performing GUI manipulation on the display screen shown in FIG. 2.

FIGS. 2 and 3 show schematically two exemplary display screens obtained with the display device 10. Both displays represent the diagnostic image of a knee as supplied from the diagnostic apparatus R. The menu region indicated by A and consisting of a title bar, a menu bar and a tool bar is shown at a brightness whose maximum value is not higher than the ordinary maximum luminance whereas the image indicated by B is shown at a brightness whose maximum value is not higher than the image maximum luminance. Since the ordinary maximum luminance is lower than the image maximum luminance, the menu region is displayed at a lower brightness than the image.

In the present invention, if the size of the image being displayed is so small that there occurs a blank area in the image-assigned region, the blank area is preferably rendered in black (as a shadow) in order to enhance the visibility of the image. If a desktop is to be displayed, the assigned area may also be rendered in black.

In this environment, the mouse 28 or other input device is operated to click at FILE in the menu bar with a cursor (pointer) 32, whereupon a pull-down menu for the FILE is displayed as shown in FIG. 3. Needless to say, this pull-down menu is displayed at a brightness not higher than the ordinary maximum luminance.

The type of display format described above is GUI. If an operation by GUI is performed in the invention, the entire display screen including not only the non-image information such as menus and characters but also the image may be represented at a brightness not higher than the ordinary maximum luminance. If a highly bright display occurs during the operation by GUI, the display screen is difficult to look at and satisfactory maneuverability cannot sometimes be attained. The practice just described above eliminates the flickering of the display screen and provides satisfactory maneuverability.

In another embodiment of the invention, the entire display screen may normally be represented at a brightness not higher than the ordinary maximum luminance and in response to an operation with the keyboard 26 or the mouse 28, only the image is displayed at a brightness not higher than the image maximum luminance.

In the examples described above, the image area of a display screen is represented at a brightness not higher than the image maximum luminance whereas non-image areas such as the menu region are displayed at a brightness not higher than the ordinary maximum luminance. This is not the sole case of the invention and the entire display screen may be switched between display at a brightness not higher than the image maximum luminance and display at a brightness not higher than the ordinary maximum luminance.

As in the foregoing examples, if the entire display screen is occupied by the image or images, it is in principle represented at a brightness not higher than the image maximum luminance but if it is entirely occupied by the non-image information such as menus, characters and others, it is displayed at a brightness not higher than the ordinary maximum luminance. The difference is that if both image and non-image information such as menus occur in a display screen, the entire display screen may at first be represented at a brightness not higher than the ordinary maximum luminance and then, in response to an operator's action, the entire display screen is switched between display at a brightness not higher than the image maximum luminance and display at a brightness not higher than the ordinary maximum luminance.

The operator's action, or the method of switching the brightness of display, is not limited in any particular way and a dedicated luminance switch (or switches) provided in the display device 10 may be used to switch between the two displays. Alternatively, GUI may be performed with the keyboard 26 or the mouse 28.

If the entire display screen is occupied by the image or the non-image information such as menus in the embodiment under consideration, the applicable maximum luminance may be selected automatically; alternatively, the entire display screen is at first represented at a brightness not higher than the ordinary maximum luminance or the image maximum luminance and then, switching between brightness levels of display may exclusively be performed in response to an operator's action. Needless to say, the embodiment where the applicable maximum luminance is selected automatically may be so adapted that the brightness of display is switched from one level to another by an operator's action.

The embodiment under consideration may also be modified to be such that the entire display screen is adjusted to a brightness not higher than the ordinary maximum luminance in response to an operation by GUI.

The method of adjusting the brightness of display in accordance with the image maximum luminance or the ordinary maximum luminance is not limited in any particular way. One applicable method is by adjusting the image data; for example, on the basis of the data supplied from the PC 24, the display control unit 18 distinguishes between an image and non-image information such as a menu and adjusts the image data accordingly so that the non-image information such as a menu is displayed at a brightness not higher than the ordinary maximum luminance.

Take, for example, the case where the display device 10 represents an image at a gradation resolution of 10 bits, with image data 1023 representing white (a highlight) and image data 0 representing black (a shadow). Display of an image at the image maximum luminance is represented by image data 0-1023 whereas display of non-image information such as menus and characters at the ordinary maximum luminance is represented by image data 0-102 or 0-127 after image data transformation in the display control unit 18. As a result, the brightness of the display of non-image information such as menus at the ordinary maximum luminance can be reduced to about a tenth or an eighth of the brightness of image display. The transformation of image data may be performed with PC 24.

If a non-light-emissive display is illuminated with the backlight unit 14 as in the illustrated case of the LCD, the backlight may be adjusted to control the brightness of display in accordance with the image maximum luminance or the ordinary maximum luminance. For example, on the basis of the data supplied from the PC 24, the light source control unit 20 distinguishes between an image and non-image information such as menus and the respective drivers 16a of the light source drive unit 16 are accordingly instructed to increase the quantity of light from the light source 30 so that an image is displayed at a high brightness equal to the image maximum luminance whereas the quantity of light from the light source 30 is reduced so that non-image information is displayed at a low brightness equal to the ordinary maximum luminance.

Adjustment of the quantity of light may be effected by adjusting the current to be supplied from the respective drivers 16a of the light source drive unit 16 to the respective light sources or by adjusting the density (number) of light sources 30 to be turned on. Both methods may be used in combination.

In addition to brightness adjustment by controlling the quantity of light, the non-emissive display apparatus 10 having the backlight unit 14 may also perform brightness adjustment by controlling the image data.

In the display device 10 of the invention, the image maximum luminance is not limited to any particular value and may be set as appropriate for the specific use of the display device. If it is to be used as a monitor for the illustrated case of (medical) diagnostic apparatus R, the image maximum luminance is preferably in the range of 200 cd/m$^2$-10,000 cd/m$^2$, more preferably between 400 cd/m$^2$ and 6,000 cd/m$^2$, most preferably between 600 cd/m$^2$ and 4,000 cd/m$^2$.

The ordinary maximum luminance associated with non-image information such as characters and menus may take on the same values as adopted by conventional display apparatus which lie, for example, between 40 cd/m$^2$ and 400 cd/m$^2$, preferably between 80 cd/m$^2$ and 200 cd/m$^2$.

The display device 10 of the invention may be connected to a plurality of diagnostic apparatus R. In this case, the brightness of display that is preferred for image-based diagnoses and other purposes often varies from one diagnostic apparatus to another. To cope with this situation, the display device of the invention is preferably adapted to have a plurality of image maximum luminance levels and, optionally, a plurality of ordinary maximum luminance levels so that the brightness of display (maximum luminance) can be switched according to the diagnostic apparatus R which is supplying a particular diagnostic image.

Brightness switching based on the diagnostic apparatus R may be performed either with a dedicated luminance switch in the display device 10, or by GUI using the keyboard 26 or the mouse 28, or automatically on the basis of recognition of the diagnostic apparatus R which is supplying the image data. Brightness adjustment may be performed by any one of the methods already described above.

While the display apparatus of the invention has been described above in detail, it should be noted that the invention is by no means limited to the foregoing examples and various improvements and modifications may of course be made without departing from the scope and spirit of the invention.

As described above in detail, the display device of the invention can provide a display at the appropriate brightness depending upon the graphics to be displayed (whether it is an image or non-image information such as characters or menus)

or in accordance with the operation done by the viewer. If it is typically used as a monitor for medical diagnostic apparatus, correct diagnosis on the basis of bright enough images can be accomplished with good maneuverability but without undue stress on the viewer's eyes.

What is claimed is:

1. A display device, having:
   at least two sets of maximum luminance including an image maximum luminance for displaying an image and an ordinary maximum luminance for displaying non-image information, said ordinary maximum luminance being lower than said image maximum luminance,
   wherein said display device is operable to simultaneously display the image at the image maximum luminance and the non-image information at the ordinary maximum luminance and a visibility of the non-image information is not reduced when displayed at ordinary maximum luminance,
   wherein an entire display screen is adjusted to a brightness of display not higher than said ordinary maximum luminance in accordance with an operation using graphical user interfaces, and
   wherein the image is displayed at a maximum luminance level for the display represented by n bits and wherein the non-image information is displayed at a maximum level represented by n–3 bits or less than n–3 bits.

2. The display device according to claim 1, further having a luminance adjusting unit which, when the non-image information is displayed in cases of display of only the image, or display of a mixture of the image and the non-image information, or display of only the non-image information, adjusts a brightness of the display in an area of the non-image information or in an entire display screen in accordance with said ordinary maximum luminance.

3. The display device according to claim 1, further having a luminance switching unit which switches a brightness of display in an entire display screen to either adjustment depending on said ordinary maximum luminance or adjustment depending on said image maximum luminance.

4. The display device according to claim 3, wherein said luminance switching unit has a selection unit which makes adjustment to the brightness of the display depending on said image maximum luminance in a case of display of only the image and makes adjustment to the brightness of display depending on said ordinary maximum luminance in a case of display of only the non-image information and which also selects the brightness of display depending on said ordinary maximum luminance and the brightness of display depending on said image maximum luminance.

5. The display device of claim 3, wherein the display screen simultaneously displays the image and the non-image information.

6. The display device of claim 3, wherein said luminance switching unit switches the brightness of the display in the entire display screen depending on if a means for pointing shown in the display screen is at an image area or at a non-image information area of the display screen.

7. The display device of claim 3, wherein an area of the display screen not displaying the image and the non-image information is rendered in black.

8. The display device according to claim 1, wherein adjustment of a brightness of display in relation to said ordinary maximum luminance and said image maximum luminance is performed by adjustment of either a light source for display or image data or both.

9. The display device of claim 1, wherein the non-image information comprises textual information.

10. The display device of claim 1, wherein the non-image information is displayed at a maximum level represented by n–3 bits.

11. The display device of claim 1, wherein adjustment of brightness of display in relation to said ordinary maximum luminance and said image maximum luminance is performed by adjustment of a light source for display.

12. The display device of claim 11, wherein adjustment of the light source comprises increasing or decreasing current through the light source.

13. The display device of claim 12, wherein the light source comprises multiple light sources.

14. The display device of claim 13, further comprising a light source control unit which controls current through each of the multiple light sources independently to increase brightness in a region of a display screen or in an entire display screen.

15. The display device of claim 14, wherein said display device receives a control signal supplied externally to distinguish image and non-image information for display and adjusting brightness of the display based on the control signal.

16. The display device of claim 15, wherein the control signal determines a type of image signal received in the display device, and the brightness is automatically adjusted for image and non-image areas based on the control signal.

17. The display device of claim 1, wherein said display device receives a control signal supplied externally to distinguish image and non-image information for display and adjusts a brightness of the display based on the control signal.

18. The display device of claim 1, wherein an adjustment of brightness of display in relation to said ordinary maximum luminance and said image maximum luminance is performed by adjustment of a plurality of light sources for display, further comprising a light source control unit which controls current through each of the plurality of the light sources independently to change brightness in a region of a display screen and to maintain brightness in another region of the display screen.

19. The display device of claim 18, wherein the region of the display screen corresponds to one of the image and the non-image information and the another region of the display screen corresponds to another of the image and the non-image information.

20. The display device of claim 19, wherein the region and the another region are displayed substantially simultaneously.

21. The display device of claim 20, wherein the region is entirely displayed at one of the image maximum luminance and the ordinary maximum luminance and the another region is entirely displayed at another of the image maximum luminance and the ordinary maximum luminance.

22. The display device of claim 1, further having a plurality of ordinary maximum luminance levels corresponding to respective one of a plurality diagnostic apparatuses connected to the display device.

23. The display device of claim 1, wherein said image maximum luminance and ordinary maximum luminance are in units of candela/$m^2$.

24. The display device of claim 1, wherein a brightness of a display of the non-image information at the ordinary maximum luminance is less than a brightness of a display of the image without any loss of gradation resolution of the non-image information.

25. The display device of claim 1, wherein when the image and the non-image information are displayed, a brightness of an entire display screen is adjusted to one of the ordinary maximum luminance and the image maximum luminance.

26. The display device of claim 25, wherein the switching between the ordinary maximum luminance and the image maximum luminance is automatically performed depending on if a means for pointing shown in the display screen is at an image area or at a non-image area information area of the display screen.

27. The display device of claim 1, wherein when the image and the non-image information are displayed simultaneously, a brightness of an entire display screen is switched between the ordinary maximum luminance and the image maximum luminance.

28. The display device of claim 1, wherein when the image and the non-image information are displayed simultaneously, a brightness of an entire display screen is adjusted to the ordinary maximum luminance.

29. The display device of claim 1, wherein said image that is displayed at the maximum luminance level is a medical image for medical diagnostic, and said display device is a medical image display device for a medical diagnostic apparatus.

30. A display device, having:
   at least two sets of maximum luminance including an image maximum luminance for displaying an image and an ordinary maximum luminance for displaying non-image information, said ordinary maximum luminance being lower than said image maximum luminance,
   wherein said display device receives a control signal supplied externally to distinguish image and non-image information for display and adjusting brightness of the display based on the control signal,
   wherein the control signal determines a type of image signal received in the display device and the image maximum luminance is set to one of a first image maximum luminance and a second image maximum luminance, wherein said first image maximum luminance and the second image maximum luminance are different from each other and are different from the ordinary maximum luminance, said image maximum luminance being set according to the control signal,
   wherein an entire display screen is adjusted to a brightness of display not higher than said ordinary maximum luminance in accordance with an operation using graphical user interfaces, and
   wherein the image is displayed at a maximum luminance level for the display represented by n bits and wherein the non-image information is displayed at a maximum level represented by n−3 bits or less than n−3 bits.

31. A display device, having:
   at least two sets of maximum luminance including an image maximum luminance for displaying an image and an ordinary maximum luminance for displaying non-image information, said ordinary maximum luminance being lower than said image maximum luminance,
   wherein the image maximum luminance is substantially in the range of 400 cd/m$^2$-10,000 cd/m$^2$ and the ordinary maximum luminance is substantially in the range of 40 cd/m$^2$-400 cd/m$^2$,
   wherein an entire display screen is adjusted to a brightness of display not higher than said ordinary maximum luminance in accordance with an operation using graphical user interface, and
   wherein the image is displayed at a maximum luminance level for the display represented by n bits and wherein the non-image information is displayed at a maximum level represented by n−3 bits or less than n−3 bits.

32. A display device, having:
   at least two sets of maximum luminance including an image maximum luminance for displaying an image and an ordinary maximum luminance for displaying non-image information, said ordinary maximum luminance being lower than said image maximum luminance,
   wherein said display device receives a control signal supplied externally to distinguish image and non-image information for display and adjusts brightness of the display based on the control signal, wherein the control signal determines a type of image signal received in the display device and the image maximum luminance is set to one of a first image maximum luminance and a second image maximum luminance, wherein said first image maximum luminance and the second image maximum luminance are different from each other and are different from the ordinary maximum luminance, and wherein said image maximum luminance is set according to the control signal,
   wherein an entire display screen is adjusted to a brightness of display not higher than said ordinary maximum luminance in accordance with an operation using graphical user interface, and
   wherein the image is displayed at a maximum luminance level for the display represented by n bits and wherein the non-image information is displayed at a maximum level represented by n−3 bits or less than n−3 bits.

33. A display device, having:
   at least two sets of maximum luminance including an image maximum luminance for displaying an image and an ordinary maximum luminance for displaying non-image information, said ordinary maximum luminance being lower than said image maximum luminance,
   wherein a brightness of a display of the non-image information at the ordinary maximum luminance is reduced to a value about equal to an eighth or less than an eighth of a brightness of a display of the image, and
   wherein an entire display screen is adjusted to a brightness of display not higher than said ordinary maximum luminance in accordance with an operation using graphical user interface, and
   wherein the image is displayed at a maximum luminance level for the display represented by n bits and wherein the non-image information is displayed at a maximum level represented by n−3 bits or less than n−3 bits.

34. A display device, having:
   at least two sets of maximum luminance including an image maximum luminance for displaying an image and an ordinary maximum luminance for displaying non-image information, said ordinary maximum luminance being lower than said image maximum luminance,
   wherein, if a size of said image being displayed is so small that there occurs a blank area in an image-assigned region, said blank area is rendered in black in order to enhance the visibility of said image,
   wherein an entire display screen is adjusted to a brightness of display not higher than said ordinary maximum luminance in accordance with an operation using graphical user interface, and
   wherein the image is displayed at a maximum luminance level for the display represented by n bits and wherein the non-image information is displayed at a maximum level represented by n−3 bits or less than n−3 bits.

35. A display device, having:

at least two sets of maximum luminance including an image maximum luminance for displaying an image and an ordinary maximum luminance for displaying non-image information, said ordinary maximum luminance being lower than said image maximum luminance, wherein the image is shown at a brightness whose maximum value is not higher than said image maximum luminance and said non-image information is shown at a brightness whose maximum value is not higher than said ordinary maximum luminance, wherein an entire display screen is adjusted to a brightness of display not higher than said ordinary maximum luminance in accordance with an operation using graphical user interface, and wherein the image is displayed at a maximum luminance level for the display represented by n bits and wherein the non-image information is displayed at a maximum level represented by n−3 bits or less than n−3 bits.

* * * * *